United States Patent [19]
Hettiarachchi et al.

[11] Patent Number: 5,805,653
[45] Date of Patent: Sep. 8, 1998

[54] NOBLE METAL DOPING OR COATING OF CRACK INTERIOR FOR STRESS CORROSION CRACKING PROTECTION OF METALS

[75] Inventors: Samson Hettiarachchi, Menlo Park; Robert Lee Cowan, II, Livermore; Thomas Pompilio Diaz, San Martin; Gary Paul Wozadlo, Los Gatos, all of Calif.

[73] Assignee: General Electric Company, Schenectady, N.Y.

[21] Appl. No.: 729,020

[22] Filed: Oct. 10, 1996

Related U.S. Application Data

[62] Division of Ser. No. 209,572, Mar. 10, 1994, Pat. No. 5,600,691.

[51] Int. Cl.[6] ................................................. G21C 9/00
[52] U.S. Cl. ............................................ 376/305; 376/306
[58] Field of Search ................................. 376/305, 306, 376/301; 422/11, 14, 19; 427/5, 6; 428/670, 685

[56] References Cited

U.S. PATENT DOCUMENTS

| | | | |
|---|---|---|---|
| 3,023,085 | 2/1962 | McBride et al. | 376/301 X |
| 4,013,559 | 3/1977 | Fernholz et al. | 210/151 |
| 4,111,830 | 9/1978 | Bannister | 422/19 X |
| 5,035,875 | 7/1991 | Daish | 376/301 X |
| 5,100,673 | 3/1992 | Eisch et al. | 424/451 |
| 5,130,080 | 7/1992 | Niedrach | 376/305 |
| 5,130,081 | 7/1992 | Niedrach | 376/305 |
| 5,135,709 | 8/1992 | Andresen et al. | 376/305 |
| 5,164,152 | 11/1992 | Kim et al. | 376/305 |
| 5,321,730 | 6/1994 | Eckardt | 376/301 |
| 5,581,588 | 12/1996 | Andresen | 376/306 |

FOREIGN PATENT DOCUMENTS

| | | |
|---|---|---|
| 0265723 | 5/1988 | European Pat. Off. . |
| 0450440 | 10/1991 | European Pat. Off. . |
| 0450444 | 10/1991 | European Pat. Off. . |
| 0514089 | 11/1992 | European Pat. Off. . |
| 0526160 | 2/1993 | European Pat. Off. . |
| 9218665 | 10/1992 | WIPO . |

OTHER PUBLICATIONS

Kowalczyk et al., "Characterization of Palladium Acctylacetonate . . . ", 3rd Symposium on Chemical Perspectives of Microelectronics Material, Boston, USA, Nov. 30–Dec. 3, 1992, Mat. Res. Soc. Symp. Proc., vol. 282, pp. 353–358.

Derwent Publications Ltd., London, GB, AN 84–059353 & JP–A–59 016 (Katayama Kagaku Kogyo Kenkyushi), Abstract.

Abernathy, C. R. et al. *Chemical Perspectives of Microelectronic Material III*, Boston, USA, Nov. 30–Dec. 3, 1992, Mat. Res. Soc. Symp. Proc., vol. 282, pp. 353–358.

Derwent Publication Ltd., London, GB; AN 84–059353 & JP–A–59 016 983 (Katayama et al. Abstract), Jan. 1984.

3rd Symposium on Chemical Perspectives of Microelectronics Material, Boston, USA, Nov. 30–Dec. 3, 1992, Mat. Res. Soc. Symp. Proc. vol. 282, pp. 353–358, Kowalczyk et al., Characterization of Palladium Acetylacetonate as a CVD Precursor for Pd Metallizat, Nov. 1992.

*Primary Examiner*—Michael J. Carone
*Assistant Examiner*—Matthew J. Lattig
*Attorney, Agent, or Firm*—Nixon & Vanderhye

[57] ABSTRACT

A method for mitigating crack growth on the surface of stainless steel or other metal components in a water-cooled nuclear reactor. A compound containing a noble metal, e.g., palladium, is injected into the water of the reactor in the form of a solution or suspension. This compound has the property that it decomposes under reactor thermal conditions to release ions/atoms of the noble metal which incorporate in or deposit on the interior surfaces of the crack. The compound may be organic, organometallic (e.g., palladium acetylacetonate) or inorganic in nature. The palladium deposited inside a crack should exhibit catalytic behavior even if the bulk surface palladium is depleted under high fluid flow conditions. As a result, the electrochemical potential inside the crack is decreased to a level below the critical potential to protect against intergranular stress corrosion cracking.

4 Claims, 6 Drawing Sheets

NOBLE METAL DOPING OR COATING OF CRACK INTERIOR FOR STRESS CORROSION CRACKING PROTECTION OF METALS

This is a Rule 60 Divisional of application Ser. No. 08/209,572, filed 10 Mar. 1994, now U.S. Pat. No. 5,600,691.

FIELD OF THE INVENTION

This invention relates to reducing the corrosion potential of components exposed to high-temperature water. As used herein, the term "high-temperature water" means water having a temperature of about 150° C. or greater, steam, or the condensate thereof. High-temperature water can be found in a variety of known apparatus, such as water deaerators, nuclear reactors, and steam-driven power plants.

BACKGROUND OF THE INVENTION

Nuclear reactors are used in electric power generation, research and propulsion. A reactor pressure vessel contains the reactor coolant, i.e. water, which removes heat from the nuclear core. Respective piping circuits carry the heated water or steam to the steam generators or turbines and carry circulated water or feedwater back to the vessel. Operating pressures and temperatures for the reactor pressure vessel are about 7 MPa and 288° C. for a boiling water reactor (BWR), and about 15 MPa and 320° C. for a pressurized water reactor (PWR). The materials used in both BWRs and PWRs must withstand various loading, environmental and radiation conditions.

Some of the materials exposed to high-temperature water include carbon steel, alloy steel, stainless steel, and nickel-based, cobalt-based and zirconium-based alloys. Despite careful selection and treatment of these materials for use in water reactors, corrosion occurs on the materials exposed to the high-temperature water. Such corrosion contributes to a variety of problems, e.g., stress corrosion cracking, crevice corrosion, erosion corrosion, sticking of pressure relief valves and buildup of the gamma radiation-emitting Co-$\alpha$ isotope.

Stress corrosion cracking (SCC) is a known phenomenon occurring in reactor components, such as structural members, piping, fasteners, and welds, exposed to high-temperature water. As used herein, SCC refers to cracking propagated by static or dynamic tensile stressing in combination with corrosion at the crack tip. The reactor components are subject to a variety of stresses associated with, e.g., differences in thermal expansion, the operating pressure needed for the containment of the reactor cooling water, and other sources such as residual stress from welding, cold working and other asymmetric metal treatments. In addition, water chemistry, welding, crevice geometry, heat treatment, and radiation can increase the susceptibility of metal in a component to SCC.

It is well known that SCC occurs at higher rates when oxygen is present in the reactor water in concentrations of about 1 to 5 ppb or greater. SCC is further increased in a high radiation flux where oxidizing species, such as oxygen, hydrogen peroxide, and short-lived radicals, are produced from radiolytic decomposition of the reactor water. Such oxidizing species increase the electrochemical corrosion potential (ECP) of metals. Electrochemical corrosion is caused by a flow of electrons from anodic to cathodic areas on metallic surfaces. The ECP is a measure of the thermodynamic tendency for corrosion phenomena to occur, and is a fundamental parameter in determining rates of, e.g., SCC, corrosion fatigue, corrosion film thickening, and general corrosion.

In a BWR, the radiolysis of the primary water coolant in the reactor core causes the net decomposition of a small fraction of the water to the chemical products $H_2$, $H_2O_2$, $O_2$ and oxidizing and reducing radicals. For steady-state operating conditions, equilibrium concentrations of $O_2$, $H_2O_2$, and $H_2$ are established in both the water which is recirculated and the steam going to the turbine. This concentration of $O_2$, $H_2O_2$, and $H_2$ is oxidizing and results in conditions that can promote inter-granular stress corrosion cracking (IGSCC) of susceptible materials of construction. One method employed to mitigate IGSCC of susceptible material is the application of hydrogen water chemistry (HWC), whereby the oxidizing nature of the BWR environment is modified to a more reducing condition. This effect is achieved by adding hydrogen gas to the reactor feedwater. When the hydrogen reaches the reactor vessel, it reacts with the radiolytically formed oxidizing species on metal surfaces to reform water, thereby lowering the concentration of dissolved oxidizing species in the water in the vicinity of metal surfaces. The rate of these recombination reactions is dependent on local radiation fields, water flow rates and other variables.

The injected hydrogen reduces the level of oxidizing species in the water, such as dissolved oxygen, and as a result lowers the ECP of metals in the water. However, factors such as variations in water flow rates and the time or intensity of exposure to neutron or gamma radiation result in the production of oxidizing species at different levels in different reactors. Thus, varying amounts of hydrogen have been required to reduce the level of oxidizing species sufficiently to maintain the ECP below a critical potential required for protection from IGSCC in high-temperature water. As used herein, the term "critical potential" means a corrosion potential at or below a range of values of about $-230$ to $-300$ mV based on the standard hydrogen electrode (SHE) scale. IGSCC proceeds at an accelerated rate in systems in which the ECP is above the critical potential, and at a substantially lower or zero rate in systems in which the ECP is below the critical potential. Water containing oxidizing species such as oxygen increases the ECP of metals exposed to the water above the critical potential, whereas water with little or no oxidizing species present results in an ECP below the critical potential.

Corrosion potentials of stainless steels in contact with reactor water containing oxidizing species can be reduced below the critical potential by injection of hydrogen into the feedwater. For adequate feedwater hydrogen addition rates, conditions necessary to inhibit IGSCC can be established in certain locations of the reactor. Different locations in the reactor system require different levels of hydrogen addition. Much higher hydrogen injection levels are necessary to reduce the ECP within the high radiation flux of the reactor core, or when oxidizing cationic impurities, e.g., cupric ion, are present.

It has been shown that IGSCC of Type 304 stainless steel (containing 18–20% Cr, 8–10.5 Ni and 2% Mn) used in BWRs can be mitigated by reducing the ECP of the stainless steel to values below $-0.230$ V(SHE). An effective method of achieving this objective is to use HWC. However, high hydrogen additions, e.g., of about 200 ppb or greater, that may be required to reduce the ECP below the critical potential, can result in a higher radiation level in the steam-driven turbine section from incorporation of the short-lived N-16 species in the steam. For most BWRs, the amount of hydrogen addition required to provide mitigation of IGSCC of pressure vessel internal components results in an increase in the main steam line radiation monitor by a factor of five to eight. This increase in main steam line radiation can cause high, even unacceptable, environmental dose rates that can require expensive investments in shielding and radiation exposure control. Thus, recent investigations have focused on using minimum levels of hydrogen to achieve the benefits of HWC with minimum increase in the main steam radiation dose rates.

An effective approach to achieve this goal is to either coat or alloy the stainless steel surface with palladium or any other noble metal. The presence of palladium on the stainless steel surface reduces the hydrogen demand to reach the required IGSCC critical potential of −0.230 V(SHE). The techniques used to date for palladium coating include electroplating, electroless plating, plasma deposition and related high-vacuum techniques. Palladium alloying has been carried out using standard alloy preparation techniques. Both of these approaches are ex-situ techniques in that they cannot be practiced while the reactor is in operation.

U.S. Pat. No. 5,135,709 to Andresen et al. discloses a method for lowering the ECP on components formed from carbon steel, alloy steel, stainless steel, nickel-based alloys or cobalt-based alloys which are exposed to high-temperature water by forming the component to have a catalytic layer of a noble metal. As used therein, the term "catalytic layer" means a coating on a substrate, or a solute in an alloy formed into the substrate, the coating or solute being sufficient to catalyze the recombination of oxidizing and reducing species at the surface of the substrate; and the term "noble metal" means metals from the group consisting of platinum, palladium, osmium, ruthenium, iridium, rhodium, and mixtures thereof.

In nuclear reactors, ECP is further increased by higher levels of oxidizing species, e.g., up to 200 ppb or greater of oxygen in the water, from the radiolytic decomposition of water in the core of the nuclear reactor. The method disclosed in U.S. Pat. No. 5,135,709 further comprises providing a reducing species in the high-temperature water that can combine with the oxidizing species. In accordance with this known method, high concentrations of hydrogen, i.e., about 100 ppb or more, must be added to provide adequate protection to materials out of the reactor core, and still higher concentrations are needed to afford protection to materials in the reactor core. It is also known that platinum or palladium can be added to increase the ECP of stainless steel exposed to deaerated acidic aqueous solutions, thereby forming a passive oxide layer on the stainless steel and reducing further corrosion.

The formation of a catalytic layer of a noble metal on an alloy from the aforementioned group catalyzes the recombination of reducing species, such as hydrogen, with oxidizing species, such as oxygen or hydrogen peroxide, that are present in the water of a BWR. Such catalytic action at the surface of the alloy can lower the ECP of the alloy below the critical potential where IGSCC is minimized. As a result, the efficacy of hydrogen additions to high-temperature water in lowering the ECP of components made from the alloy and exposed to the injected water is increased manyfold. Furthermore, it is possible to provide catalytic activity at metal alloy surfaces if the metal substrate of such surfaces contains a catalytic layer of a noble metal. Relatively small amounts of the noble metal are sufficient to provide the catalytic layer and catalytic activity at the surface of the metal substrate. For example, U.S. Pat. No. 5,135,709 teaches that a solute in an alloy of at least about 0.01 wt.%, preferably at least 0.1 wt.%, provides a catalytic layer sufficient to lower the ECP of the alloy below the critical potential. The solute of a noble metal can be present up to an amount that does not substantially impair the metallurgical properties, including strength, ductility, and toughness of the alloy. The solute can be provided by methods known in the art, for example by addition to a melt of the alloy or by surface alloying. In addition, a coating of the noble metal, or a coating of an alloy comprised of a solute of the noble metal as described above, provides a catalytic layer and catalytic activity at the surface of the metal. Suitable coatings can be deposited by methods well known in the art for depositing substantially continuous coatings on metal substrates, such as plasma spraying, flame spraying, chemical vapor deposition, physical vapor deposition processes such as sputtering, welding such as metal inert gas welding, electroless plating, and electrolytic plating.

Thus, lower amounts of reducing species such as hydrogen are effective to reduce the ECP of the metal components below the critical potential, because the efficiency of recombination of oxidizing and reducing species is increased manyfold by the catalytic layer. Reducing species that can combine with the oxidizing species in the high-temperature water are provided by conventional means known in the art. In particular, reducing species such as hydrogen, ammonia, or hydrazine are injected into the feedwater of the nuclear reactor.

SUMMARY OF THE INVENTION

The present invention is a method for in situ application of palladium or other catalytic metal onto a stainless steel or other metal surface immersed in high-temperature water, whereby the catalytic metal penetrates into existing cracks in the metal surface. The method comprises the step of injecting a solution or suspension of a compound containing a catalytic metal into the water of said reactor. The selected catalytic metal must have the property of increasing the corrosion resistance of the stainless steel when incorporated therein or deposited thereon. The selected compound must have the property that it decomposes under reactor thermal conditions to release ions/atoms of the selected catalytic metal which incorporate in or deposit on the oxide film formed on the reactor components. As used in the claims set forth hereinafter, the term "atom" means ions or atoms. The preferred compound for this purpose is palladium acetylacetonate, an organometallic compound. However, other noble metal compounds of organic, organometallic and inorganic nature can also be used for this purpose, such as palladium nitrate. The concentration of palladium in the reactor water is preferably in a range up to 100 ppb.

Upon injection, the palladium compound decomposes and deposits palladium on the metal surfaces immersed in the water. The palladium gets incorporated into the oxide film on stainless steel components via a thermal decomposition process of the compound wherein palladium ions/atoms apparently replace iron, nickel and/or chromium atoms in the oxide film, resulting in a palladium-doped oxide film. The oxide film is believed to include mixed nickel, iron and chromium oxides. Alternatively, palladium may be deposited within or on the surface of the oxide film in the form of a finely divided metal. This doping technique provides sufficient catalytic activity for recombining $H_2$ and $O_2$ into water that the ECP of the stainless steel surfaces is reduced to below the critical threshold ECP. This approach has been shown to be effective against crack initiation and crack growth in stainless steel at $H_2/O_2$ molar ratios greater than 2 in the high-temperature water environment.

It has been discovered that during the foregoing deposition, palladium is deposited inside any existing cracks on the reactor component surfaces. The palladium deposits around the crack mouth region and into the interior of the crack. This palladium deposition inside the crack results in crack mitigation even under sub-stoichiometric levels of hydrogen (i.e., $H_2/O_2<2$).

It has further been discovered that rapid depletion of palladium from the crack interior does not occur because of the low fluid flow experienced inside the crack even if the crack mouth is in a high fluid flow regime. This is a significant advantage because crack mitigation is still achievable even if bulk surface palladium removal occurs under high fluid flow conditions.

DETAILED DESCRIPTION OF THE PREFERRED EMBODIMENTS

Figure 1:
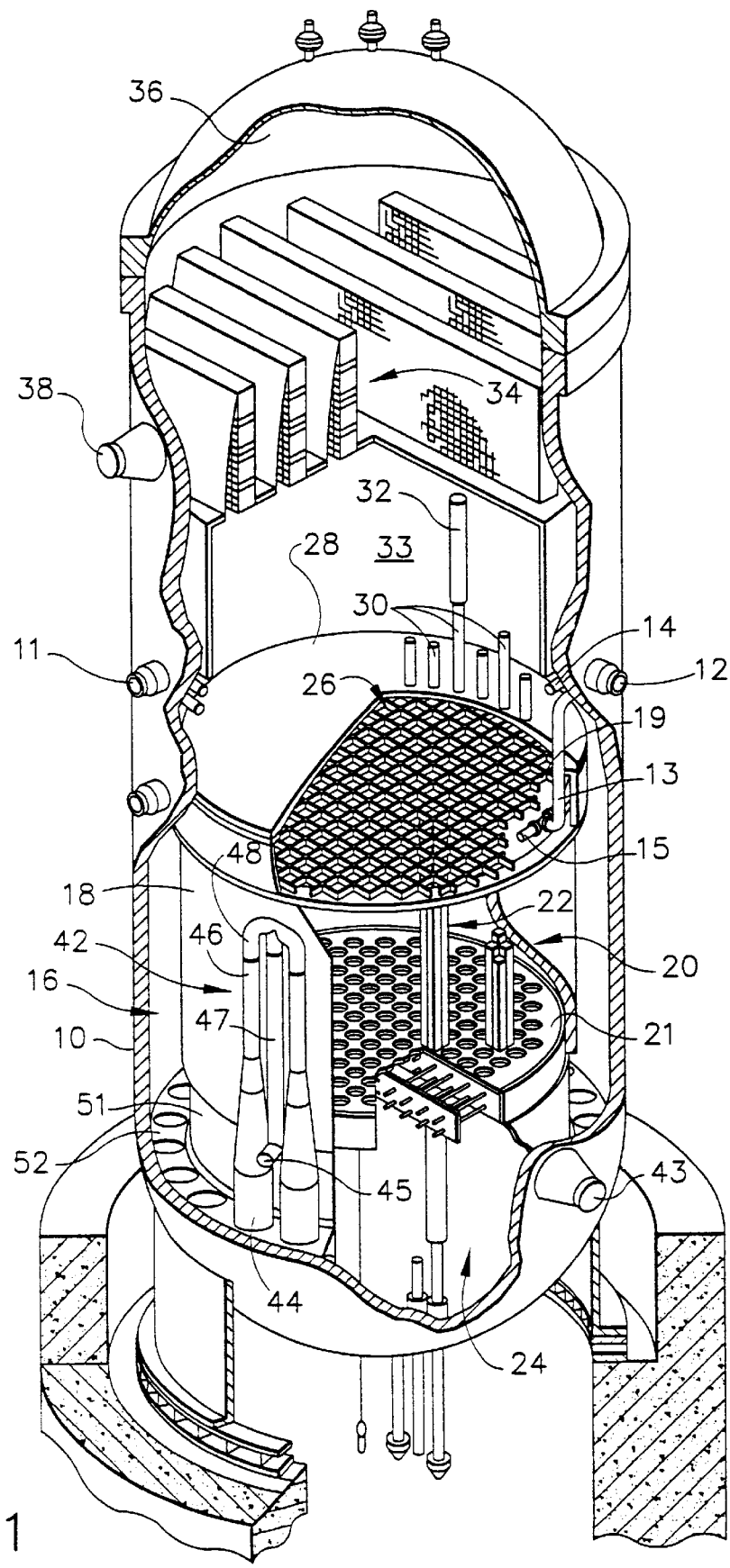
FIG. 1 is a schematic showing a partially cutaway perspective view of a conventional BWR.

The fluid flow in a boiling water reactor will be generally described with reference to FIG. 1. Feedwater is admitted into a reactor pressure vessel (RPV) 10 via a feedwater inlet 12 and a feedwater sparger 14, which is a ring-shaped pipe having suitable apertures for circumferentially distributing the feedwater inside the RPV. A core spray inlet 11 supplies water to a core spray sparger 15 via core spray line 13. The feedwater from feedwater sparger 14 flows downwardly through the downcomer annulus 16, which is an annular region between RPV 10 and core shroud 18. Core shroud 18 is a stainless steel cylinder which surrounds the core 20 comprising numerous fuel assemblies 22 (only two 2×2 arrays of which are depicted in FIG. 1). Each fuel assembly is supported at the top by top guide 19 and at the bottom by core plate 21. Water flowing through downcomer annulus 16 then flows to the core lower plenum 24.

The water subsequently enters the fuel assemblies 22 disposed within core 20, wherein a boiling boundary layer (not shown) is established. A mixture of water and steam enters core upper plenum 26 under shroud head 28. Core upper plenum 26 provides standoff between the steam-water mixture exiting core 20 and entering vertical standpipes 30, which are disposed atop shroud head 28 and in fluid communication with core upper plenum 26.

The steam-water mixture flows through standpipes 30 and enters steam separators 32, which are of the axial-flow centrifugal type. The separated liquid water then mixes with feedwater in the mixing plenum 33, which mixture then returns to the core via the downcomer annulus. The steam passes through steam dryers 34 and enters steam dome 36. The steam is withdrawn from the RPV via steam outlet 38.

The BWR also includes a coolant recirculation system which provides the forced convection flow through the core necessary to attain the required power density. A portion of the water is sucked from the lower end of the downcomer annulus 16 via recirculation water outlet 43 and forced by a centrifugal recirculation pump (not shown) into jet pump assemblies 42 (only one of which is shown) via recirculation water inlets 45. The BWR has two recirculation pumps, each of which provides the driving flow for a plurality of jet pump assemblies. The pressurized driving water is supplied to each jet pump nozzle 44 via an inlet riser 47, an elbow 48 and an inlet mixer 46 in flow sequence. A typical BWR has 16 to 24 inlet mixers.

The present invention is an in-situ technique to coat or dope the interior of cracks on reactor component surfaces with noble metal (e.g., palladium) by injecting a noble metal-containing compound into the high-temperature water of a BWR. Preferably the noble metal compound is injected at a point upstream of the feedwater inlet 12 (see FIG. 1). The high temperatures as well as the gamma and neutron radiation in the reactor core act to decompose the compound, thereby freeing noble metal ions/atoms for deposition on the oxide film surfaces around the mouth and in the interior of each crack. One noble metal-containing compound successfully used for this purpose is an organometallic compound, palladium acetylacetonate. However, other noble metal compounds of organic, organometallic and inorganic nature can also be used for this purpose, e.g., an inorganic compound such as palladium nitrate.

Tests were conducted which proved that the present method for depositing or incorporating palladium in the interior of a cracks on the stainless steel surfaces of a BWR is feasible. Moreover, it has been shown that after palladium treatment in accordance with the invention, crack growth was mitigated even in the presence of substoichiometric levels of hydrogen. It is expected that the ECP value of the stainless steel surfaces inside the cracks remain quite negative and below the required IGSCC critical potential of −0.230 V(SHE) even under conditions wherein the ECP value of stainless steel surfaces outside the cracks is above the critical potential.

Experiments were performed to determine the ECP response of Pd-doped Type 304 stainless steel by injecting an organometallic palladium compound, i.e., palladium acetylacetonate, into an autoclave that formed part of a high-temperature recirculating flow loop. The autoclave had a constant extension rate tensile (CERT) specimen made of Type 304 stainless steel and a stainless steel tip electrode also made of Type 304 stainless steel. The reference electrodes used to measure ECPs consisted of a $Cu/Cu_2O/ZrO_2$ type reference electrode and an external pressure balanced Ag/AgCl, 0.1M KCl reference electrode. The recirculating flow loop contained deionized water heated to 550° F. inside the autoclave. The oxygen level in the effluent water was 200 ppb.

The palladium acetylacetonate injection solution was prepared by dissolving 52.6 mg of palladium acetyl-acetonate powder in 40 ml of ethanol. The ethanol solution is then diluted with water. After dilution, 10 ml of ethanol are added to the solution. This is then diluted to a volume of 1 liter. Alternatively, a water-based suspension can be formed, without using ethanol, by mixing palladium acetylacetonate powder in water.

Figure 2:
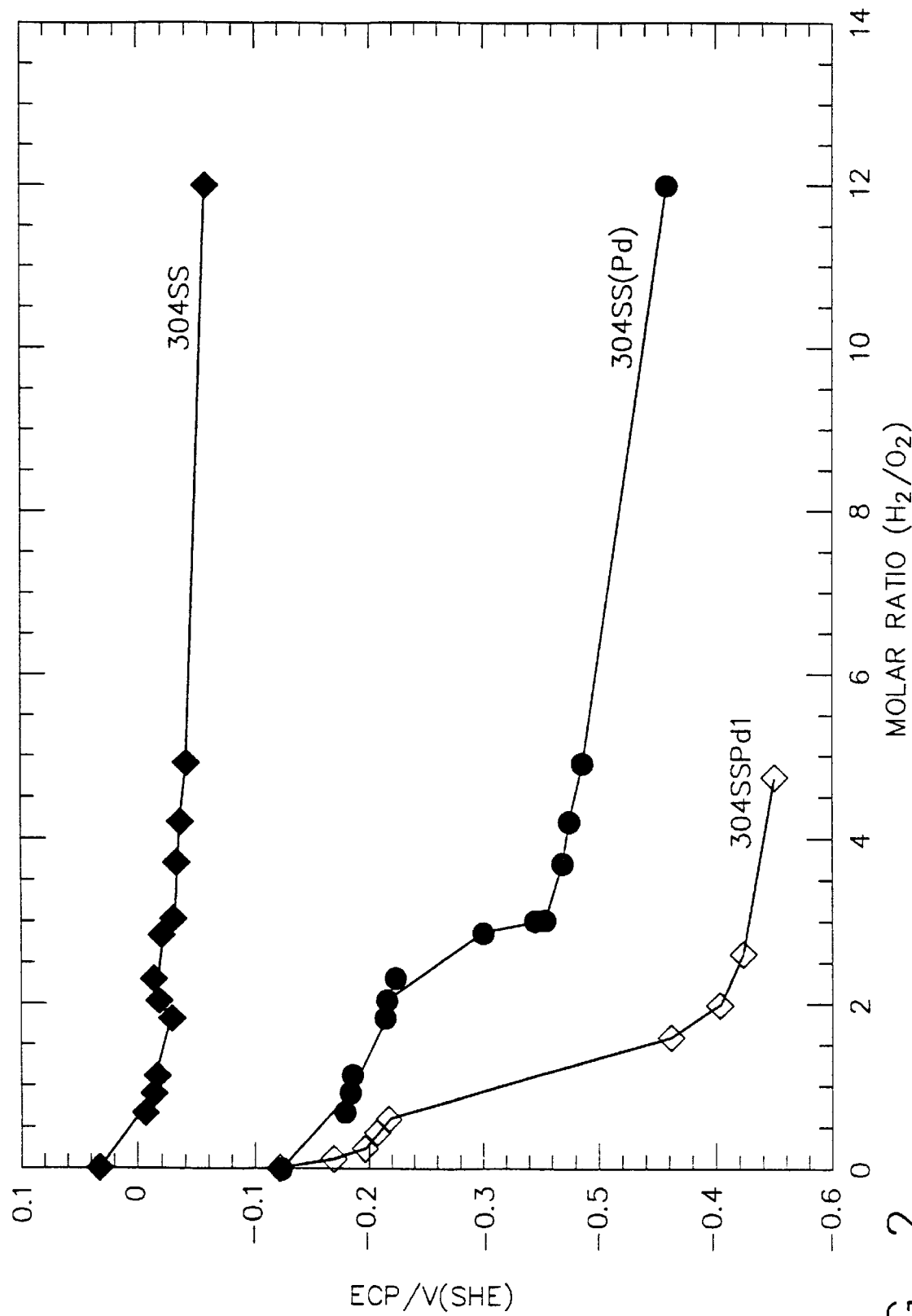
FIG. 2 is a plot showing the ECP response as a function of the molar ratio of hydrogen to oxygen for three Type 304 stainless steel specimens: 304SS—not doped with palladium; 304SS(Pd)—doped with 58 ppb Pd; and 304SSPd1—doped with 96 ppb Pd.

In one experiment, palladium acetylacetonate compound, dissolved in the ethanol/water mixture, was injected into the inlet side of the main pump in the flow loop using an injection pump at a rate so that the solution entering the autoclave (at 550° F.) had a Pd concentration of ~58 ppb. In another experiment, palladium acetylacetonate compound was injected at a rate so that the solution entering the autoclave had a Pd concentration of ~96 ppb. The results of these experiments are depicted in FIG. 2.

For the 58 ppb Pd-doped specimen, the ECP reaches a value of −0.220 V(SHE) at a $H_2/O_2$ molar ratio of 2, whereas at the same molar ratio the 96 ppb Pd-doped specimen shows an ECP of −0.520 V(SHE). The latter specimen almost behaved like a pure platinum or pure palladium specimen. Thus, palladium doping of Type 304 stainless steel can achieve the IGSCC protection potential at a $H_2/O_2$ molar ratio of 2–2.5. For the same molar ratios, the ECP of undoped Type 304 stainless steel was −0.020 V(SHE), which is considerably higher than the IGSCC protection potential of −0.230 V(SHE).

Further experiments were conducted to demonstrate the effectiveness of palladium doping in crack mitigation. Three materials were tested: Alloy 182, Alloy 600 and Type 304 stainless steel. Each specimen was doped with 96 ppb Pd. Crack growth was measured in BWR water at 550° F. having an excess of hydrogen, i.e., a $H_2/O_2$ molar ratio >2. The results of these experiments are depicted in FIGS. 3–5.

Figure 3:
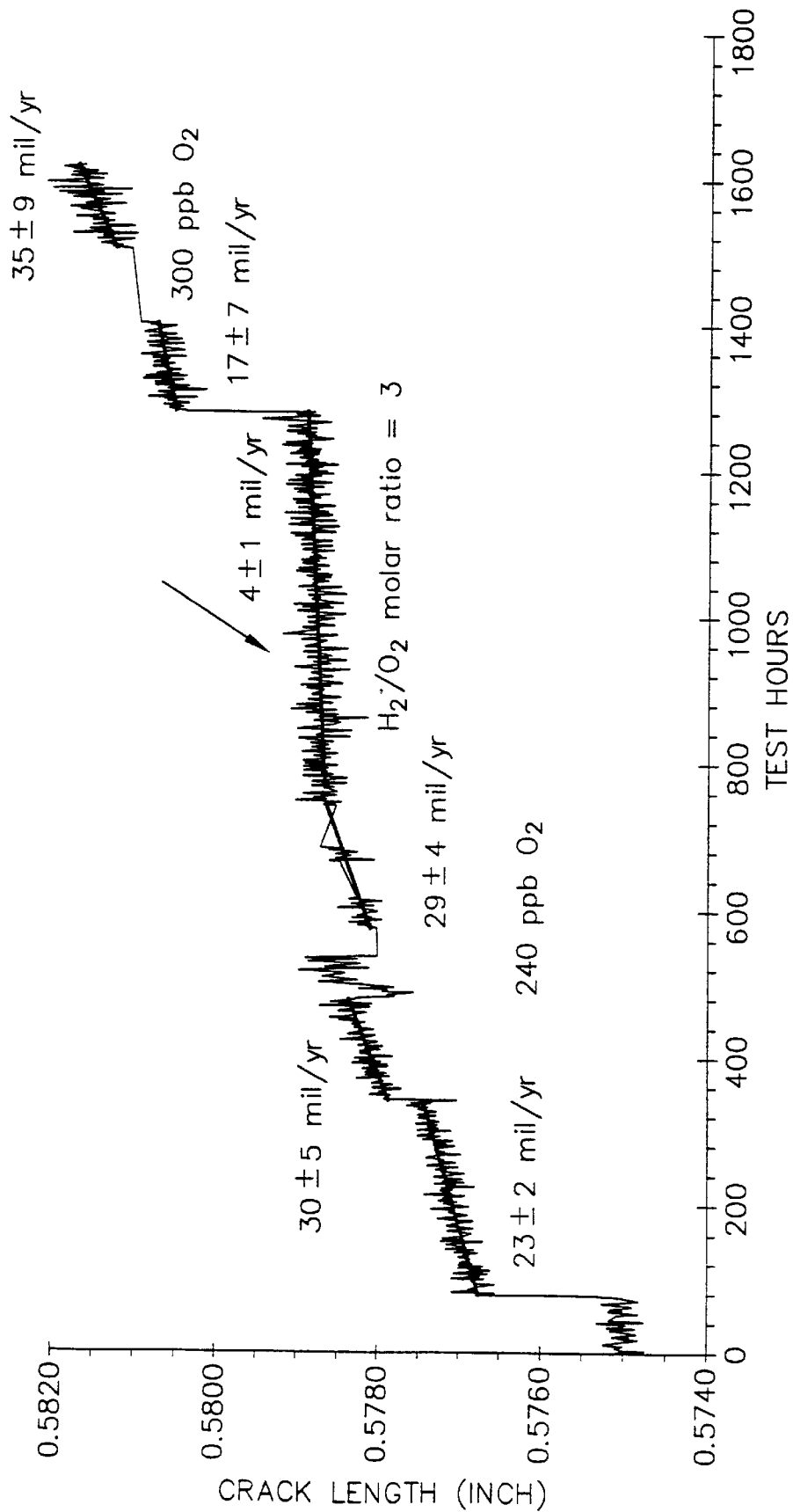
FIGS. 3, 4 and 5 illustrate the crack growth behavior in BWR water at 550° F. of specimens made of Alloy 182, Alloy 600 and Type 304 stainless steel, respectively, each of which had been doped with 96 ppb Pd.

Referring to FIG. 3, the crack growth behavior of a Pd-doped Alloy 182 (a nickel-based alloy) specimen is shown at a dissolved oxygen level of 240 ppb $O_2$ over a time period of 760 hr. During this time, the crack growth rate stabilizes at ~30 mils/yr in high-purity BWR-type water having a conductivity of ~0.170 gS/cm. The slightly higher conductivity of the water is due to the higher dissolved oxygen content. At 760 hours, $H_2$ is added to the system so that the $H_2/O_2$ molar ratio >2. Clearly, the crack growth rate (CGR) drops from ~30 mils/yr to ~4 mils/yr, and remains at this value for more than 400 hours. At 1260 hr, the $H_2$ was turned off and the system reverted back to 300 ppb $O_2$. The CGR rose to a value of ~35 mils/yr. This test results demonstrate the ability of palladium doping to mitigate the CGR of an Alloy 182 specimen with minimum hydrogen demand, i.e., at a $H_2/O_2$ molar ratio of 3.

Figure 4:
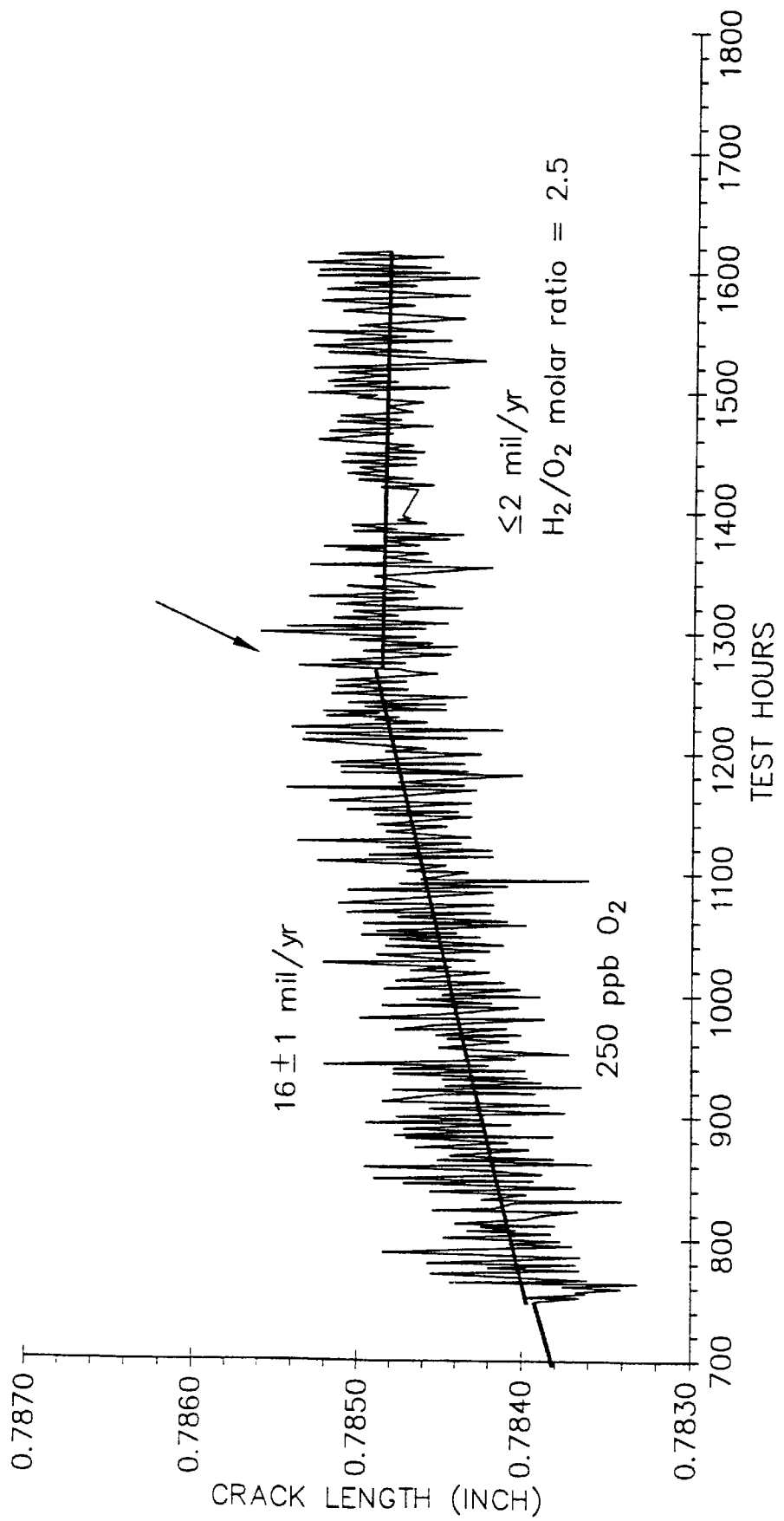

Referring to FIG. 4, a Pd-doped Alloy 600 (a nickel-chromium-iron alloy) specimen was exposed to 250 ppb $O_2$ over a time period from 750 to 1250 hr. The CGR during this period was ~16 mils/yr. When $H_2$ was introduced at 1260 hr, the CGR dropped to <2 mils/yr, demonstrating the catalytic nature of the surfaces in the crack interior, which caused the CGR to drop to very low values. The $H_2/O_2$ molar ratio at this point was 2.5. Thus, the palladium doping was effective in mitigating the CGR in Alloy 600 with minimum hydrogen demand.

Figure 5:
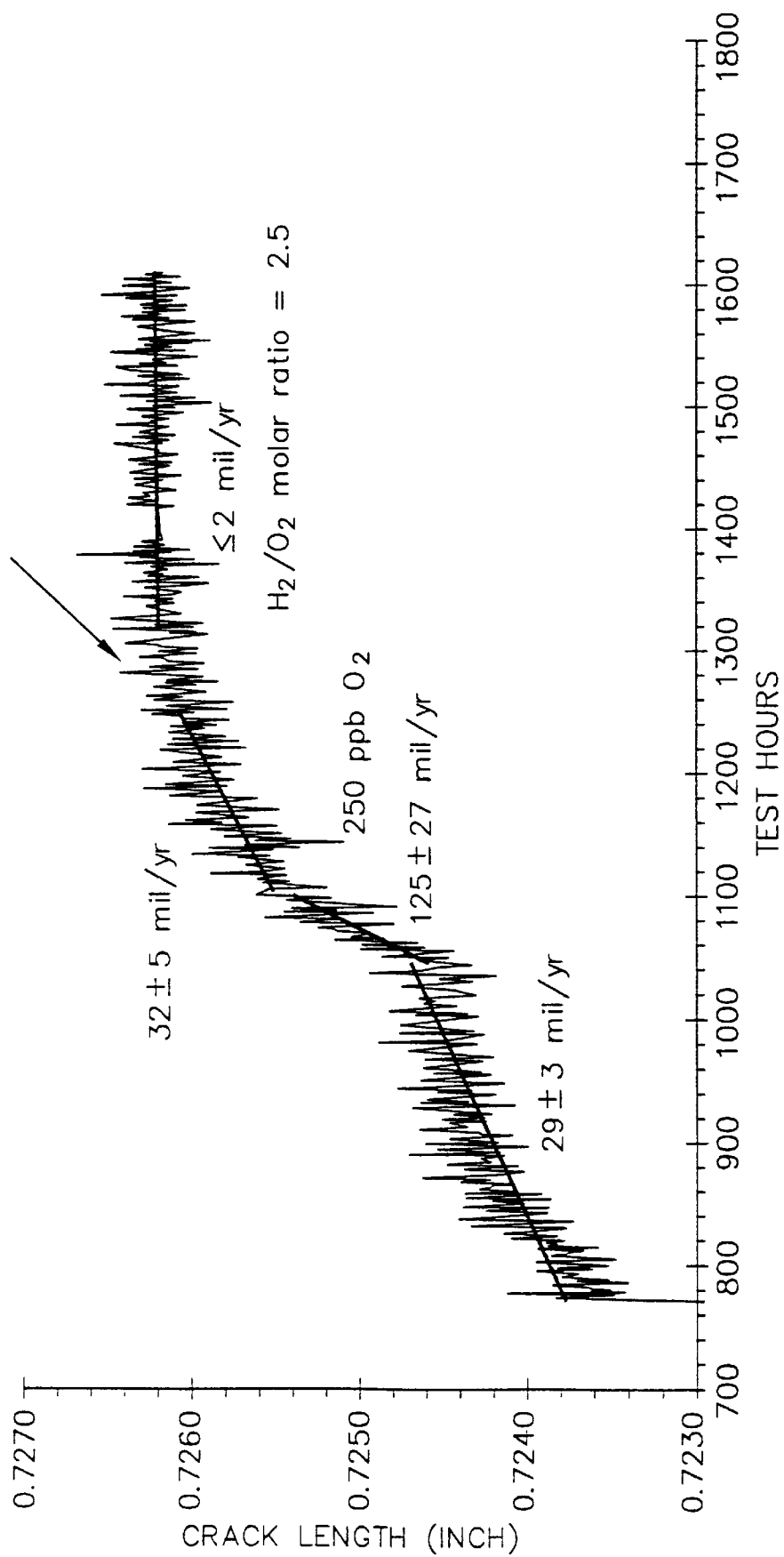

Referring to FIG. 5, a Pd-doped Type 304 stainless steel specimen was exposed to 250 ppb $O_2$ over a time period from 750 to 1250 hr. The CGR during this period was ~32 mils/yr. When $H_2$ was introduced at 1260 hr, the CGR dropped to <2 mils/yr, again showing the catalytic nature of the surfaces in the crack interior. The $H_2/O_2$ molar ratio at this point was 2.5. Thus, palladium doping was also effective in mitigating the CGR in Type 304 stainless steel with minimum hydrogen demand.

Figure 6A:
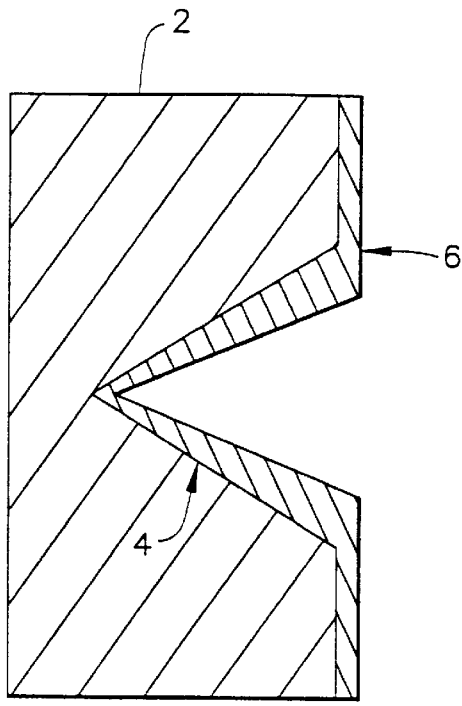
FIGS. 6A and 6B are schematics showing Pd doping of a cracked specimen before and after being subjected to high-flow conditions.
Figure 6B:
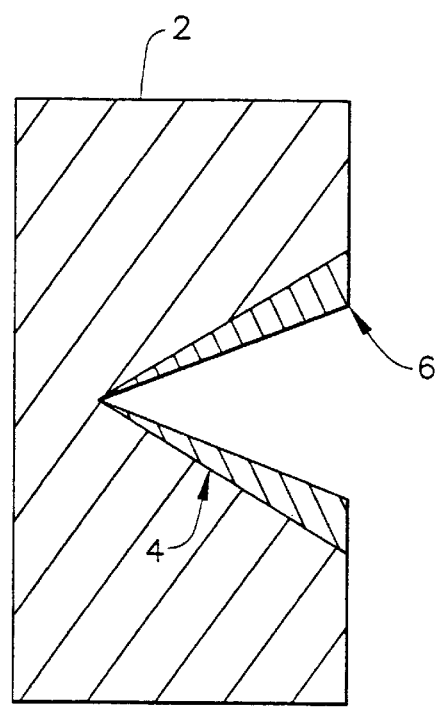

During palladium doping, palladium 6 is deposited on the exposed surfaces of a metal specimen 2 as well as inside the crack 4 on interior surfaces thereof as shown in FIG. 6A. Thus, under low-flow conditions, palladium may remain on the surfaces of components as well as inside cracks, resulting in low ECPs under excess hydrogen. This situation mitigates crack propagation as well as crack initiation as long as palladium remains on the surfaces. However, under high-flow conditions it is possible that a portion of the surface palladium may be removed by the shear flow of the fluid, as depicted in FIG. 6B. As a result, the catalytic activity of the surface may decrease. However, the CGR will not increase due to the presence of palladium 6 in the crack growth region 4 in an amount which is sufficient to provide catalytic activity inside the crack. The palladium inside the crack will not be removed by the high fluid flow because the fluid inside the crack is in a quiescent state and not subject to the shear flow experience by the exposed surfaces, as shown in FIG. 6B. Thus, the palladium doping approach for crack mitigation works even under high-flow conditions such as those experienced in a BWR under excess $H_2$. The presence of palladium inside the crack mouth considerably reduces the hydrogen demand necessary for crack mitigation.

CERT test data for Pd-doped and undoped Type 304 stainless steel specimens, all of which were pre-oxidized, are compared in the following Table:

| CONSTANT EXTENSION RATE TEST DATA | | | | | | | |
|---|---|---|---|---|---|---|---|
| Specimen | $O_2$ (ppb) | $H_2$ (ppb) | $H_2/O_2$ | ECP (V,SHE) | TTF* (hr) | Max. Load (lbs.) | IGSCC (%) |
| Undoped | 180 | 25 | 2.22 | +0.010 | 144 | 565 | 25 |
| Pd-doped | 180 | 25 | 2.22 | −0.265 | 319 | 825 | 0 |
| Pre-cracked/ Pd-doped | 200 | 18 | 1.44 | −0.300 | 311 | 800 | 3 |
| Pre-cracked/ Pd-contaminated | 260 | 20 | 1.10 | −0.160 | 220 | 725 | 20 |

*TTF — total time to failure.

This test data shows that an undoped Type 304 stainless steel specimen in water with a $H_2/O_2$ molar ratio of 2.22 failed after 144 hr showing 25% IGSCC. The maximum load in this case was 565 lbs. An identical specimen, after Pd doping, failed at 319 hr showing 0% IGSCC (i.e., ductile failure). The Pd-doped specimen was able to sustain a load of 825 lbs., typical of similar specimens showing ductile failure. A pre-cracked Pd-doped specimen also showed a long failure time of 311 hr and was able to sustain a load of 800 lbs. despite the previously existing crack. The ECP in this case was −0.300 V(SHE) at a $H_2/O_2$ molar ratio of 1.44. The specimen showed 3% IGSCC, which was due to the IGSCC generated by the pre-cracking stage. This crack did not grow subsequent to palladium doping. Thus, palladium doping is effective in both preventing the initiation of intergranular stress corrosion cracks and in mitigating the already existing cracks, as shown by the above-described severe CERT test.

The last row in the table shows the results obtained with a pre-cracked and Pd-contaminated specimen. This specimen failed after 220 hr at a relatively high load of 725 lbs. despite the fact that this specimen had not been intentionally doped, but perhaps had been exposed to some trace palladium level during the precracking test, because pre-cracking was done in an autoclave that had been previously used to measure ECPs of Pd-doped specimens. The first clue that this specimen had been contaminated came from the ECP value of −0.160 V(SHE), which was considerably lower than expected for an undoped specimen in the presence of 260 ppb $O_2$. This is clear from the first row in the Table, which shows that an undoped specimen has an ECP of +0.010 V(SHE).

Figure 7A:
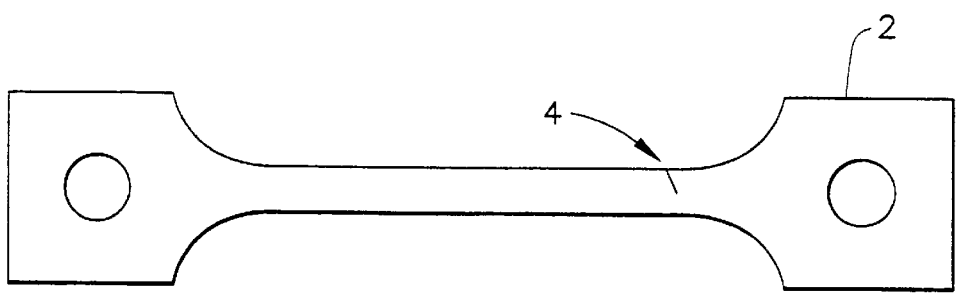
FIGS. 7A and 7B are schematics respectively showing the location of a pre-crack in a CERT specimen and the location of specimen failure after palladium contamination.

A CERT specimen made of pre-oxidized Type 304 stainless steel was pre-cracked (see FIG. 7A) at 550° F. in water containing 170 ppb $O_2$. Pre-cracking was performed at a strain rate of $4 \times 10^{-7}$/sec to a strain of 5.6%, at which point three small intergranular cracks having a width less than 20 mils were identified. A subsequent analysis revealed that these cracks were ~5–7 mils deep. After analyzing the cracks and their location in this specimen, the CERT test was continued at a $H_2/O_2$ molar ratio of 1.2 until the specimen failed after a total of 227 hr (including pre-cracking time corrected for time to reach the yield stress). The maximum load was 725 lbs. (800 to 830 lbs. would represent ductile failure) and the degree of IGSCC was 20%. The longer time to failure and the higher maximum load are both indicative of the possible palladium contamination of the specimen.

Figure 7B:
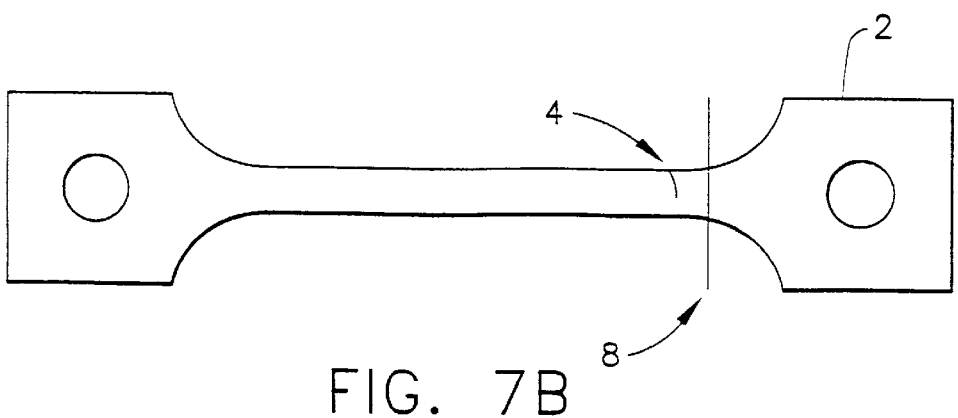

The most important observation of this test was that failure (indicated by line 8 in FIG. 7B) of the specimen 2 occurred outside the pre-cracked zone 4. A new crack had been generated, while the pre-existing cracks did not grow. This indicated that the trace Pd level that had contaminated the specimen was insufficient to prevent crack initiation, but was sufficient to mitigate an already existing crack. This result in itself proves that palladium is inside the crack. Growth of the previously existing cracks was mitigated by the palladium contamination, even though the ECP of the specimen, −0.160 V(SHE), was considerably more positive than the generally accepted IGSCC protection potential of −0.230 V(SHE). Since the pre-existing crack did not grow and since failure occurred outside the pre-crack region, it is reasonable to infer that palladium inside the crack provided the necessary protection potential for mitigating crack growth under excess hydrogen.

To provide protection against IGSCC by depositing palladium or other catalytic metal (e.g., other noble metals) inside a crack formed in the surface of a component operating in high-temperature water has heretofore been unknown. The palladium deposited inside a crack in accordance with the present invention should exhibit catalytic behavior even if the bulk surface palladium is depleted under high fluid flow conditions. Furthermore, any palladium that gets inside a crack is expected to last longer than the bulk surface palladium because of the absence of shear flow inside a crack.

The foregoing method has been disclosed for the purpose of illustration. Variations and modifications of the disclosed method will be readily apparent to practitioners skilled in the art of hydrogen water chemistry. For example, noble metals other than palladium can be applied using this technique. A noble metal can be injected in the form of an organic or organometallic compound to reduce the potential of reactor components made of stainless steel or other IGSCC-susceptible alloy even in the absence of hydrogen injection. Alternatively, the noble metal can be injected in the form of an inorganic compound in conjunction with hydrogen injection to reduce the ECP of reactor components. One option is to inject the palladium acetylacetonate solution or suspension via the same port by which dissolved hydrogen is injected. Furthermore, the metal acetylacetonate need not be injected as part of an ethanol/water solution. Instead the metal acetylacetonate powder can be mixed with water alone to form a suspension which is injected into the reactor water. To improve the stability of the suspension, it is obvious that ultrasonication can be used to break down the particles. An alternative application technology includes having the noble metal compound as pressed pellets in a basket hung inside the reactor at different locations and operating the reactor with pump heat until noble metal doping occurs. Another approach would be to inject noble metal-containing compound locally into areas that have a higher susceptibility to IGSCC. All such variations and modifications are intended to be encompassed by the claims set forth hereinafter.

We claim:

1. A metal component not created with a noble end having a crack on a surface thereof, said crack having an oxided interior surface in which atoms of a noble metal are incorporated, said noble metal having the property of decreasing the electrochemical chemical potential of said metal component surface when incorporated in said oxided surface, said noble metal being present in an amount such that when said metal component surface is immersed in high-temperature water, the electochemical chemical potential inside said crack is less than the critical potential to protect against intergranular stress corrosion cracking.

2. The metal component as defined in claim 1, wherein said metal component is made of stainless steel.

3. The metal component as defined in claim 1, wherein said noble metal is palladium.

4. A metal component having a crack with an oxided interior surface thereof, wherein propagation of said crack has been mitigated by a method comprising filling said crack with high-temperature water in which a compound containing a noble metal is dissolved, and causing said noble metal compound to decompose in said high-temperature water to release atoms of said noble metal which incorporate in said oxided surface.

* * * * *